United States Patent [19]

Phillips

[11] Patent Number: 5,443,529
[45] Date of Patent: Aug. 22, 1995

[54] PROSTHETIC DEVICE INCORPORATING MULTIPLE SOLE BLADDERS

[76] Inventor: Van L. Phillips, 5499 Maravillas, Rancho Santa Fe, Calif. 92067

[21] Appl. No.: 23,897

[22] Filed: Feb. 19, 1993

Related U.S. Application Data

[63] Continuation-in-part of Ser. No. 951,857, Sep. 28, 1992, abandoned, which is a continuation of Ser. No. 662,783, Feb. 28, 1991, Pat. No. 5,290,319.

[51] Int. Cl.⁶ .............................................. A61F 2/66
[52] U.S. Cl. ........................................ 623/56; 623/55; 36/29
[58] Field of Search ................... 623/56, 55, 53, 54; 36/29, 35 B

[56] References Cited

U.S. PATENT DOCUMENTS

| | | |
|---|---|---|
| 508,034 | 11/1893 | Moore . |
| 951,989 | 3/1910 | Hanger . |
| 1,352,943 | 9/1920 | Dodge . |
| 1,498,838 | 6/1924 | Harrison, Jr. . |
| 1,596,923 | 8/1926 | Cooney . |
| 1,649,773 | 11/1927 | Witmyer . |
| 1,804,915 | 5/1931 | Collins . |
| 2,126,654 | 8/1938 | Morris . |
| 2,128,134 | 8/1938 | Giusto ................... 36/29 X |
| 2,197,093 | 1/1939 | Campbell . |
| 3,475,836 | 11/1969 | Brahm . |
| 4,217,705 | 8/1980 | Donzis . |
| 4,319,412 | 3/1982 | Muller et al. . |
| 4,358,902 | 11/1982 | Cole et al. . |
| 4,397,104 | 8/1983 | Doak . |
| 4,414,760 | 11/1983 | Faiella . |
| 4,446,634 | 5/1984 | Johnson et al. . |
| 4,547,913 | 10/1985 | Phillips . |
| 4,610,099 | 9/1986 | Signori . |
| 4,633,597 | 1/1987 | Shiang . |
| 4,670,995 | 6/1987 | Huang . |
| 4,744,157 | 5/1988 | Dubner . |
| 4,763,426 | 8/1988 | Polus et al. . |
| 4,822,363 | 4/1989 | Phillips . |
| 4,959,073 | 9/1990 | Merlette . |
| 4,991,317 | 2/1991 | Lakic . |
| 4,994,086 | 2/1991 | Edwards . |
| 5,025,575 | 6/1991 | Lakic . |
| 5,037,444 | 8/1991 | Phillips . |
| 5,108,456 | 4/1992 | Coonan, III . |
| 5,156,631 | 10/1992 | Merlette . |
| 5,181,932 | 1/1993 | Phillips . |
| 5,181,933 | 1/1993 | Phillips . |

FOREIGN PATENT DOCUMENTS

| | | |
|---|---|---|
| 0379849 | 8/1923 | Germany . |
| 22172 | of 1898 | United Kingdom . |
| 120462 | 11/1918 | United Kingdom . |
| 275902 | 8/1927 | United Kingdom . |

*Primary Examiner*—David H. Willse
*Attorney, Agent, or Firm*—Knobbe, Martens, Olson & Bear

[57] ABSTRACT

The invention relates to a prosthetic device utilizing multiple bladders to absorb, store and release energy. In particular, the present invention relates to a prosthetic foot and leg device having a foot member extending from the heel end to the toe end and having a sole, wherein two or more bladders are secured to the bottom of said sole, to provide a smooth roll-over transition from heel-strike to toe-off. Generally, the bladders do not extend the length of the sole, so that the migration of air at heel-strike or toe-load is eliminated. Moreover, the bladders are positioned with one or more cavities therein, permitting the bladders to expand laterally inward and outward which advantageously provides stability and balance to the amputee.

16 Claims, 9 Drawing Sheets

FIG. 11
FIG. 12
FIG. 13
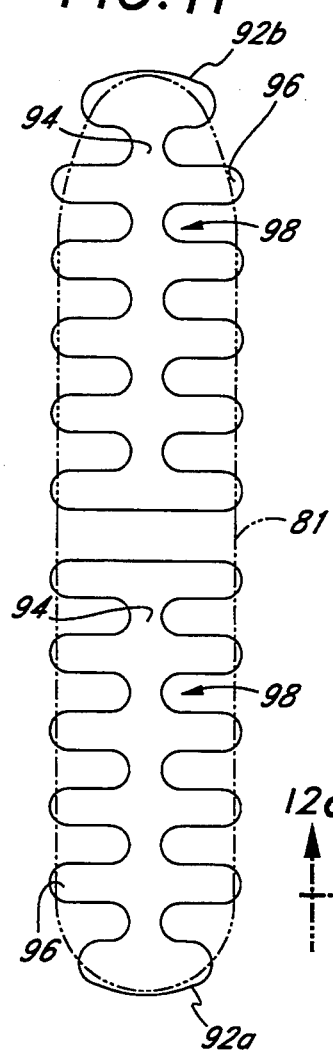
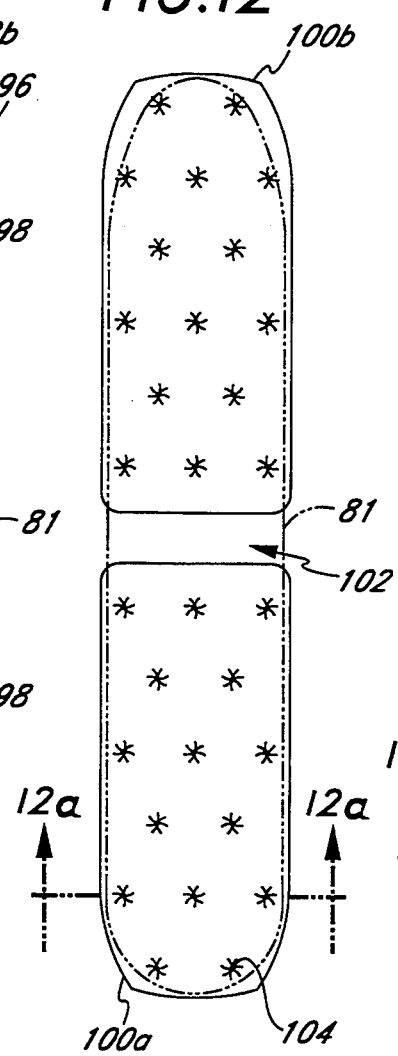
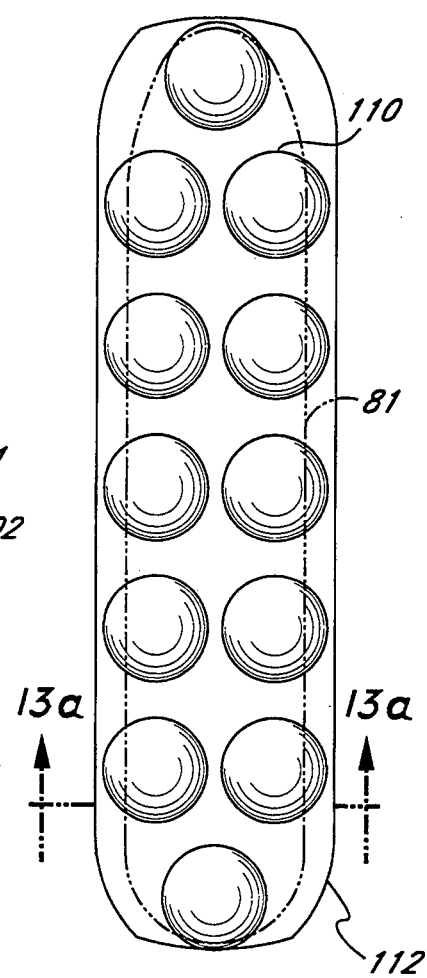
FIG. 12a
FIG. 13a
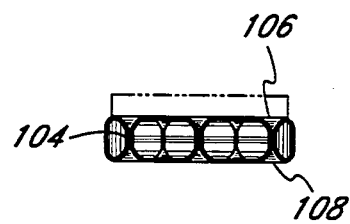
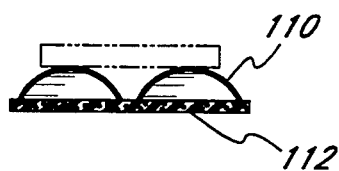

PROSTHETIC DEVICE INCORPORATING MULTIPLE SOLE BLADDERS

This is a continuation-in-part of U.S. application Ser. No. 07/951,857, filed Sep. 28, 1992, now abandoned, which is a continuation of U.S. application Ser. No. 07/662,783, filed Feb. 28, 1991, now U.S. Pat. No. 5,290,319.

FIELD OF THE INVENTION

The present invention relates to prosthetic devices, and in particular, prosthetic devices incorporating multiple bladders on the sole to provide energy absorption, storage and release.

BACKGROUND OF THE INVENTION

With the ever-increasing number of amputees needing prosthetic devices, various types of foot and leg prostheses have been developed. In the past, prosthetic devices usually comprised of some form of artificial limb or rod extending to the ground merely to support body weight. More recently, other devices have been made to imitate the structure of the human foot and leg, as well as to simulate their natural movement. Many consisted of a hinge to allow movement between the leg and foot.

The gross inadequacies of these type of devices became readily apparent as they tended to be bulky, heavy, non-resilient, and provided little or no energy absorption, storage and release. As such, the amputee's activity level was severely limited. As a result, it was unheard of for amputees to participate in sporting activities such as tennis, basketball, jogging and skiing.

Various improvements to prosthetic devices have enabled the amputee to substantially increase his or her activity level. A prosthetic foot and leg device which allows a high degree of mobility on the part of an amputee was disclosed in my U.S. Pat. No. 4,457,913 entitled "Composite Prosthetic Foot and Leg." That patent disclosed a prosthetic foot and leg device utilizing a resin impregnated high strength filament structure for the leg portion, foot portion and heel portion, with all three regions being provided with substantial elastic flexibility, of relatively low energy absorption characteristics, so as to give the wearer high mobility with a relatively natural feel. Additional improvements have been made to prosthetic devices to greatly enhance the lifelike movement of the foot, and to improve the adjustability and interchangeability of the devices to custom fit various amputee weights, gaits, activity levels and other conditions unique to the individual amputee.

Such improvements are also disclosed in U.S. Pat. Nos. 4,822,363 entitled "Modular Composite Prosthetic Foot and Leg," and 5,037,444 entitled "Prosthetic Foot." In each of these patents, a substantially low energy absorbing material, utilizing a resin impregnated high strength laminate, is used in conjunction with a substantially low energy absorbing structure, comprising elongated curvilinear sections, extending from the stump of the amputee down and forward, with a heel portion extending rearward. This combination of material and structure greatly improves the wearability of the prosthetic device, and has enabled the amputee to resume substantially normal activities.

In the past, attempts have been made to utilize air cushions in various prosthetic devices, but none were designed to enhance activity levels beyond the expected sedentary levels of most amputees. In particular, none of the prior devices improved the dynamic performance of the prosthesis through the entire roll-over motion of a normal gait, i.e., the transfer of weight and motion from the initial heel strike to toe-off.

Generally, persons walk or run by transferring weight from the heel to the toe during a normal gait, with the weight being transferred from the initial heel strike, to the mid-stance, to the toe-load, and then to the toe-off. The heel-strike represents the initial contact between the heel and the ground, the mid-stance represents the period where weight is distributed over the foot, the toe-load represents the period where weight is on the front end of the foot, and toe-off represents the period immediately after pushing off. In addition, this heel-to-toe movement is constantly monitored by the person's proprioception, which helps the individual constantly adjust his or her balance, without which he or she would be prone to become off-balance.

U.S. Pat. No. 2,197,093 to Campbell discloses an air cushion located on the sole of an artificial limb to provide a pneumatic cushion arrangement for artificial feet. This structure, however, did not accommodate the normal heel-to-toe transfer of weight, from the heel strike to the toe-off. For instance, at the moment of heel strike, as the heel portion of the cushion is compressed, the air in the cushion is likely to be forced forward from the heel to the toe end. Thus, at the heel strike, the point of greatest impact, the air cushion would tend to flatten as it is compressed, and would not provide adequate support. Also, if attempts were made to cure the migration of air by inflating the cushion to a substantially high pressure, the air cushion would lose its ability to absorb and store energy, and would become too stiff to provide a smooth roll-over from heel to toe.

Therefore, there is a need for a prosthetic device having an air bladder system which addresses the entire spectrum of an amputee's normal stride.

SUMMARY OF THE INVENTION

The present invention represents a substantial improvement over the prior art prosthetic devices in that it achieves a smooth transition of weight and motion through the entire spectrum of movement of a normal gait, from heel strike to toe-off. In particular, the present invention relates to two or more air bladders positioned on the sole of the prosthesis. The present invention advantageously absorbs, stores and releases energy throughout each phase of the stride. The present invention also relates to a prosthesis that is substantially adjustable, such that the unique characteristics of each amputee, such as weight and changes in weight, size and gait, as well as particular needs, can be accommodated.

The air bladder system comprises two or more air bladders placed on the sole of the foot prosthesis. In the preferred embodiment, each of the air bladders generally have a U-shaped configuration. Each bladder is comprised of a flexible and vapor impervious inside bag, with a stretch-resistant fabric outside bag covering the inside bag. The inside bag is made by sealing two layers of material having the appropriate configuration. The outside bag is formed in the same fashion, with an opening to permit the inside bag to be positioned therein. The outside bag is sewn along the edges to hold the inside bag within the outside bag.

The present invention combines the high energy storage and release features of my other prosthetic devices, with an air bladder system comprising a novel configuration to help absorb the initial impact and springiness normally associated with high energy storing and releasing prosthesis. The preferred embodiment of the present invention incorporates two bladders (or more in other embodiments) positioned on the sole of the prosthesis, extending from the rearwardmost portion of the heel to the frontmost portion of the toe.

The separate bladders of the present invention are advantageously positioned to eliminate unwanted migration of air from one end of the prosthesis to the other. Because the present invention has a heel bladder that is separate from the toe bladder, compression of the heel bladder does not force air to migrate forward to the front of the prosthesis which would otherwise cause the resiliency of the heel portion to diminish. The toe bladder is also separate from the heel bladder so that compression exerted onto the toe does not force air to migrate backward to the heel, which would otherwise cause the toe portion to flatten out. Thus, the separation of the bladders enables sufficient pressure to be maintained at the critical heel strike and toe-load portions of the gait, such that a smooth transition is achievable. The separation also allows the heel bladder and toe bladder to be inflated separately.

The present invention also utilizes bladders which are ideally suited to provide a combination of energy absorption, storage and release. The bladder is essentially a container for a predetermined volume of air, which can be inflated to varying pressures. In use, as loads are exerted on the bladder, the bladder tends to flatten and expand outward, which momentarily increases the pressure in the bladder. Then, as the bladder is relaxed, it immediately returns to its original shape due to its flexibility, decreasing the pressure in the bladder and releasing the stored energy. The bladder's flexibility provides a buoyant resiliency which has previously been unattainable by solid energy absorbing means. Bladders also absorb and distribute energy evenly and in all directions. Thus, not only do air bladders provide a good cushion, they also give the prosthetic device controlled resiliency, which gives the amputee a lighter feel and a more energetic response.

The air bladders of the present invention are also substantially lightweight, which is critical when considering that the prosthesis is attached to the end of an amputee's stump. The lighter the prosthetic device, the easier it is for the amputee to secure the prosthetic device to the stump. A lightweight prosthesis is also easier to control, which is significant if the amputee is to participate in activities such as tennis, jogging and swimming.

The air bladder of the present invention is also well suited to conform to the various contours of prosthetic device structures, as the bladder can take on virtually any shape. Ideally, in a preferred embodiment, the bladders are substantially U-shaped, with the open ends facing inward toward each other toward the center of the sole, near the arch section. The bladders are also approximately equivalent in length, one bladder extending approximately from the center to the toe of the sole, and the other extending from the center to the heel.

One advantage to having bladders of U-shape configuration is that, upon compression, the bladders will tend to spread out, which is important in providing good energy absorption, storage and release, and in permitting the amputee to maintain balance and control. The combined U-shaped bladders essentially occupy the perimeter of the sole of the prosthetic device, with a partial cavity extending substantially longitudinally in the center of the sole. This configuration enables the bladders to spread both laterally outward along the periphery and inward toward the center when compressed, providing the amputee with a feeling of being low centered, as opposed to high centered, which can assist the amputee in retaining balance.

The front bladder also extends to the perimeter of the toe portion, with a slightly larger cavity than the heel bladder. The larger cavity is substantially located near the center of the toe area in the preferred embodiment. Again, this configuration enables the bladder to spread out both inwardly and outwardly when compressed, so as to improve energy absorption, storage and release in a relatively small area. The larger cavity in the toe bladder also provides a larger "sweet" spot for the toe-load, which corresponds to the need for slightly greater balance and flexibility in the toe.

The back to back U-shaped configurations also provide a smooth transition from heel to toe. This represents a substantial improvement over many of the prior art devices which have a break between the heel and toe, making a smooth rollover relatively impossible to achieve.

The present invention can also enable the amputee to adjust the softness or firmness of the bladders separately. In the preferred embodiment, each of the separate bladders can be adjusted independently, such that an infinite variety of performance levels can be obtained. This adjustability feature is significant when considering the infinite number of characteristics of individual amputees that must be accommodated by a prosthetic device. The present invention can accommodate amputees who are light, heavy, sedate, rigorously active, young, old, small, large, or have particular and specific needs.

For instance, on one end of the spectrum, the present invention is ideal for geriatric use because the prosthetic device is lightweight and can provide a soft, cushiony response, as if the amputee were walking on a plush, padded carpet. The adjustability of the bladders allows the geriatric amputee to adjust the cushion to suit his or her specific needs. The U-shaped configuration of the bladders also provides lateral stability, which is important to some geriatrics who neither have the strength nor coordination to remain balanced. A smooth transition from the heel strike to the toe-off, without a break, significantly enhances stability, which is important because such amputees may not have adequate strength to adjust from a break in stride, causing the geriatric amputee to become off balance or lose control of the prosthesis.

At the other end of the spectrum, the present invention is ideal for amputees who participate in rigorous sporting activities, such as jogging, tennis and basketball. Because these sporting activities generate and require significant amounts of energy, the amputee needs significant energy absorption, storage and release to permit the amputee to continue the activity for extended periods of time, resulting in greater satisfaction and enjoyment. Because these types of physical activities place great stress on the stump of the leg, the high energy absorption and storage properties of the bladders are especially well suited. The present invention is also ideal for physical activities because the prosthesis is light in weight, provides a smooth rollover without a break, and provides lateral stability, all of which all helpful in maintaining coordination and balance.

As a general rule, by keeping the pressure in the bladders relatively low, an amputee can increase energy absorption, thereby providing a softer, more cushiony feel, which improves the smoothness of the rollover transition. On the other hand, an amputee can increase the energy storage and release capabilities of the bladders by increasing the pressure in the bladders to provide more resiliency and higher performance. One can also readily see that the bladders can be adjusted independently, for instance, one bladder can be under high pressure, and the other under moderate pressure. One skilled in the art will readily see that any number of combinations are possible to suit any particular need.

Though the preferred embodiment utilizes two separate bladders, the present invention is not limited to a prosthetic device having only two bladders. The present invention also contemplates any number of inflatable containers strategically placed on the sole, which provides the benefits that have heretofore been disclosed.

In general, the two bladder system is advantageous because two is the minimum number of bladders needed to provide all of the benefits of the present invention, and, in particular, to prevent unwanted migration of air. In addition, two separate bladders of substantially equal length placed end-to-end are particularly advantageous because they obtain a proportionate balance between the need to eliminate migration of air from heel to toe, with the need to have just enough migration of air to give the amputee a better feel, which more closely imitates a person's normal proprioception. The relative size and configuration of the bladders is also advantageous, in that a wide range of pressures can be utilized to provide a wide range of performance levels.

The bladders of the present invention can also be tapered such that the bladders are thick at the rearward end of the heel portion, and tapers thin toward the toe end. A high heel and low toe may be ideal for jogging or running, while those who are relatively sedate may wish to have a flat heel and toe configuration. One of ordinary skill in the art can readily see that any configuration and shape can be utilized to provide specific advantages.

The multiple bladder system of the present invention also allows the amputee to maintain the pressure of the air bladders relatively low. In previous bladder devices, one had to pump the bladder to substantially high pressure to avoid migration of air. However, a bladder at such high pressure may be too stiff for some amputees who might desire a more cushioned feel. Moreover, a bladder under high pressure is more prone to leakage and rupture than two bladders at lower pressures.

Another advantage of the present invention is that the prosthetic device can be utilized without the bladders, or with the bladders deflated. This is significant because in some situations the bladders may become damaged or punctured, causing the bladders to deflate. The present invention utilizes an energy storing prosthesis, as disclosed in my previous patents and patent applications, which can be used in conjunction with the bladder system of the present invention, so the amputee may continue to move quite normally notwithstanding the deflation of one or more bladders.

Another advantage of the present invention is that the air bladders can be manufactured at a relatively low cost and that they allow the prosthetic device to be manufactured inexpensively. In fact, the performance of the air bladders is good enough that the other components of the prosthetic device need not be substantially flexible and high in energy storage and release for the prosthetic device to provide adequate smooth rollover and feel. Thus, the present invention is ideal for low cost applications of prosthetic devices, but can also be incorporated into advanced high performance prosthetic devices.

BRIEF DESCRIPTION OF THE DRAWINGS

FIGS. 8-12 are plan views of alternative air bladder configurations.

FIG. 12a is a cross-sectional view taken on lines 12a, 12a of FIG. 12.

FIG. 13 is a bottom plan view of a further alternative air bladder configuration with a prosthetic device shown in phantom and a padding member.

FIG. 13a is a cross-sectional view taken along lines 13a, 13a of FIG. 13.

DETAILED DESCRIPTION OF THE INVENTION

The present invention relates to a prosthetic device utilizing multiple air bladders positioned on the sole, which are utilized in conjunction with a prosthetic device having high energy storage and release characteristics, such as those disclosed in my previous patents and pending applications. In particular, the present invention relates to a sole bladder system utilizing two or more separate bladders positioned from the rearwardmost portion of the heel to the frontmost portion of the toe to provide a smooth roll-over from heel to toe.

Foot Prosthesis

Figure 1:
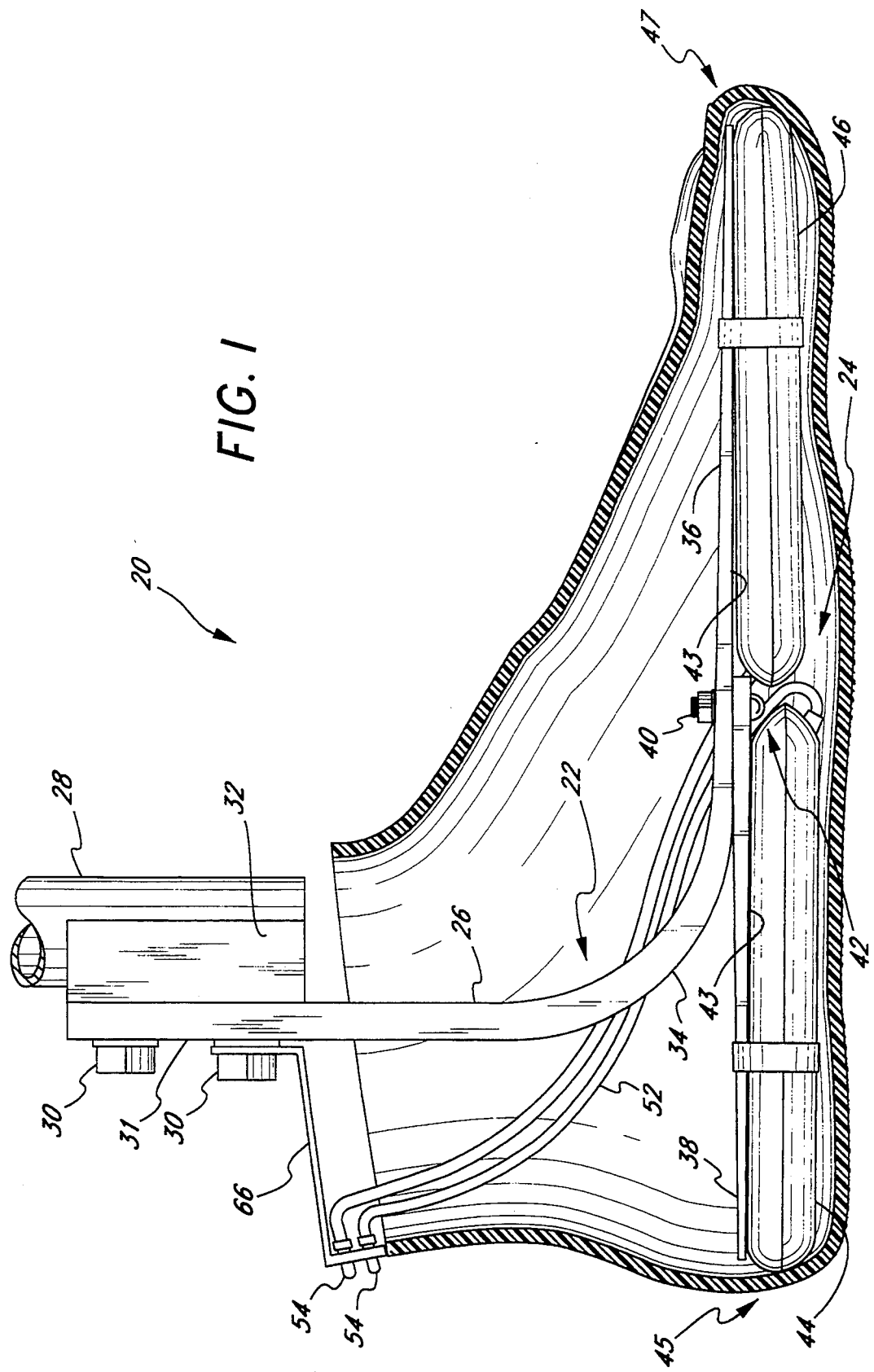
FIG. 1 is a side elevational view of a prosthesis incorporating the preferred air bladder system of the present invention and illustrating an outer cosmesis shown cut away.

As can be seen in FIG. 1, the prosthesis 20 of the present invention comprises a prosthetic device 22 with an inflatable air bladder system 24. The prosthetic device 22 structure, as previously stated, can be any of the various prosthetic devices disclosed in my previous patents and pending applications, or any other prosthetic device having a sole member extending substantially from heel to toe.

In the preferred embodiment, as shown in FIG. 1, the prosthetic device 22 structure comprises a curvilinear foot portion 26 extending downward from a pylon member 28 which extends from the stump of the amputee (not shown). The foot portion 26 is secured to the pylon member 28 by two or more bolts 30, which extend through the upper extremity 31 of the foot portion, and through an attachment connector 32 which conforms to the outer surface of the pylon. The foot portion 26 extends downward and forward therefrom, bending about an ankle section 34. The foot portion 26 also extends from the ankle section 34 forward to a toe end 36 of the prosthesis. Also, attached to the underside of the foot portion 26 is a heel portion 38 extending rearward therefrom. In the preferred embodiment, the foot portion 26 is an integral member formed from superimposed laminates utilizing a resin impregnated high-strength filament structure as disclosed in my previous U.S. Pat. Nos. 4,547,913; 4,822,363; and 5,037,444, the relevant parts of which are incorporated herein by reference. The heel portion 38 is also made of the same material.

In the preferred embodiment, as shown in FIG. 1, the foot portion 26 and heel portion 38 are secured together by a nut and bolt combination 40, wherein the heel portion can be removed from the foot portion if necessary. A mid-foot sole region 42 comprising both the foot portion 26 and heel portion 38 is arranged such that it extends along substantially the same plane, forming a relatively flat bottom sole surface 43 upon which the air bladder system 24 of the present invention is secured.

Air Bladder System

The air bladder system 24 of the present invention comprises two or more separate air bladders positioned on the sole of the foot prosthesis, as can be seen in FIG. 1. In the preferred embodiment, a heel bladder 44 is secured to the heel portion 38 of the prosthesis, and a toe bladder 46 is secured to the toe portion 36 of the foot prosthesis.

Figure 2:
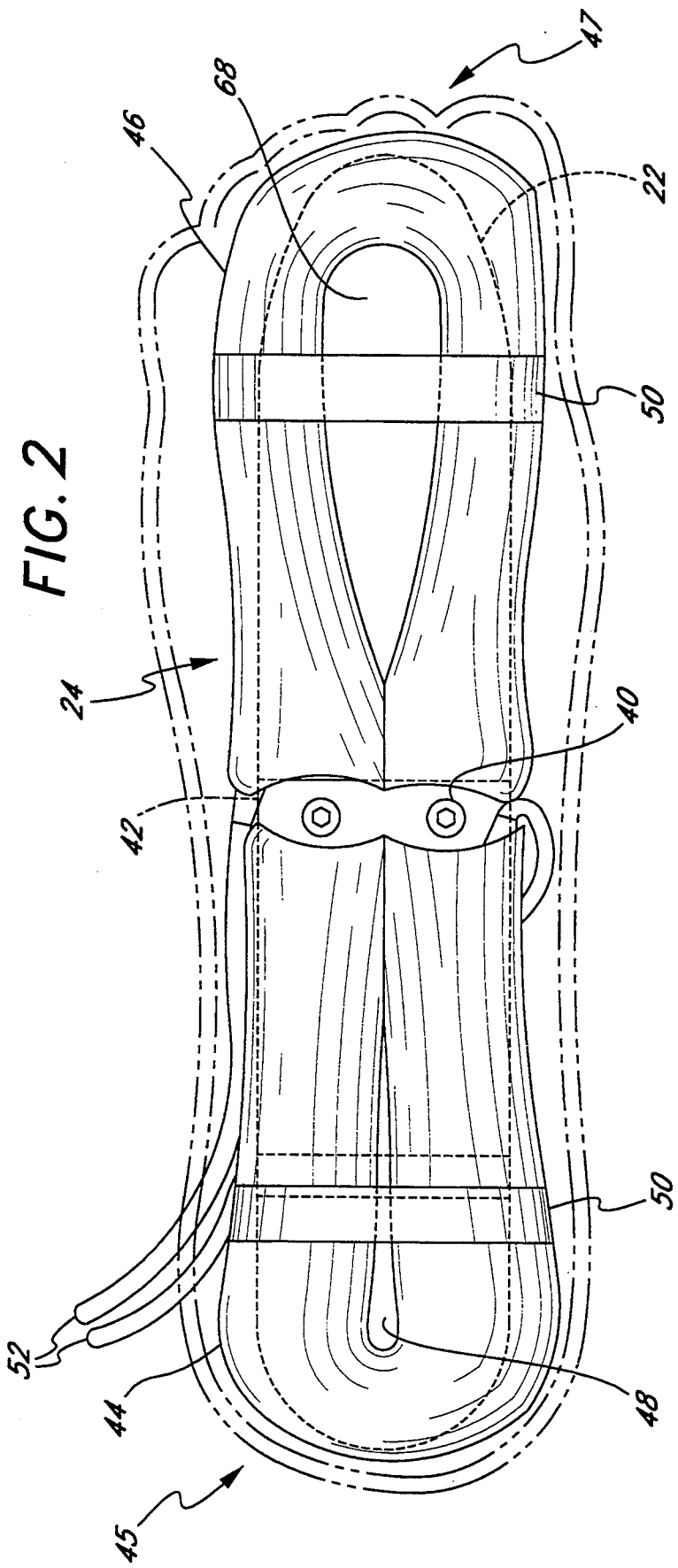
FIG. 2 is a bottom view of the air bladder system of FIG. 1 with the cosmesis shown in phantom.
Figure 3:
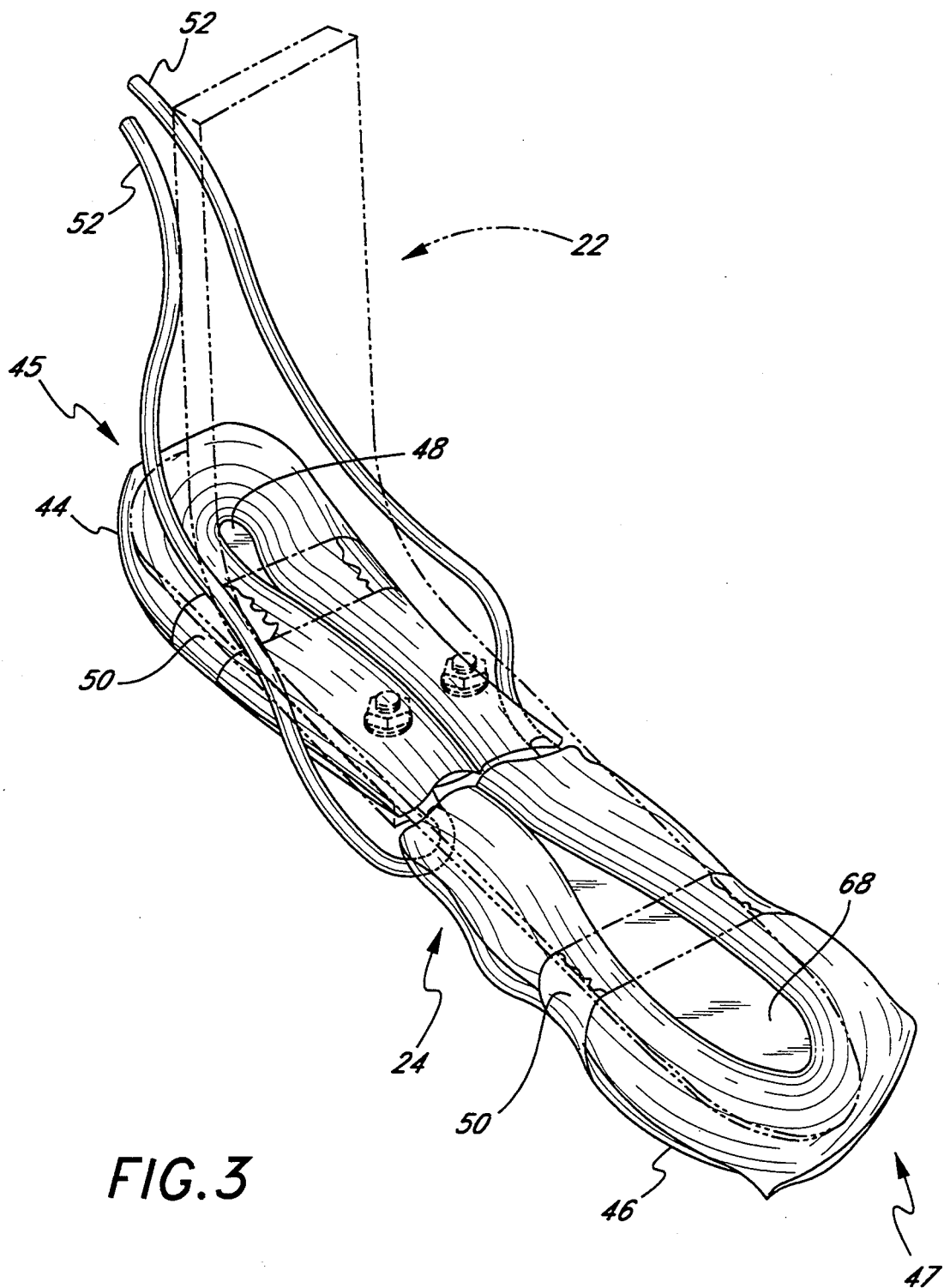
FIG. 3 is a perspective view of the air bladder system of FIG. 1 with a prosthetic device shown in phantom.

As can best be seen in FIGS. 2 and 3, the air bladders 44, 46 of the present invention are generally of U-shaped configuration, such that the open end of the U-shape of each air bladder faces inward toward the center of the sole 42 of the prosthesis. This configuration effectively places the air bladders 44, 46 around the perimeter of the sole surface 43, which provides substantial support to the prosthesis around the entire periphery of contact between the prosthesis and the ground. Unlike the prior art prostheses, the present invention utilizes an air bladder system 24 which provides resilience throughout the entire motion of a normal gait, from the rearwardmost end of the heel to the forwardmost end of the toe. This air bladder system therefore provides a smooth roll-over from the heel-strike to toe-off, providing a relatively break-free transition of weight and motion.

The U-shape configuration of the heel bladder 44 is also uniquely designed to provide the amputee with increased lateral stability. As shown in FIGS. 2 and 3, the heel bladder 44 has a cavity 48 substantially in the center of the heel. This configuration permits the heel bladder 44 to spread, both laterally outward and laterally inward toward the cavity 48 when compressed, giving the amputee better side support and a feeling of being low centered, as opposed to being high centered. One skilled in the art will readily see that other configurations may provide the same benefits discussed herein.

As can be seen in FIGS. 2 and 3, the heel bladder 48 resembles an inflatable tube being bent at its center, although it is actually a bag within a bag seamed in the appropriate configuration, as will be discussed in more detail. This configuration permits a cavity 48 to be formed between the ends 63 of the bladder. The toe bladder 46 likewise has a similar configuration and appearance, with the exception that the cavity 68 is slightly larger.

Because the bladders are manufactured out of sheets of material, however, as will be discussed later, each of the bladders 44, 46 have seams along the edge of the perimeter where the materials are sealed together. Because the materials are also sealed together along the inside cavities 48, 68, a seam is also found along the inside edge of the cavities 48, 68. The material in the cavities 48, 68 can either be cut away or can be left in place.

The bladders can also be inflated to various pressures, depending upon the needs of the amputee. The amount of pressure within the bladders 44, 46 also determines its relative thickness and its capacity to absorb, store and release energy.

The thickness of the bladders 44, 46 can also be varied by making the air bladders 44, 46 either larger or smaller. The larger the bladder is constructed, the greater the amount of air it can contain, and thereby the greater the thickness of the bladder. The thickness of the bladders 44, 46 can also vary from end to end by varying the relative size of the bladder along any point thereof.

The length and size of the bladders 44, 46 can also vary, although in the preferred embodiment, the toe bladder 46 and the heel bladder 44 are approximately the same length and occupy approximately the same overall area of the sole.

The air bladders 44, 46 of the present invention are secured to the foot prosthesis 22 preferably by a bonding agent such as glue, or with bands of elastic material 50, which are flexible, yet retain the bladders relatively securely against the sole. It is noted, however, that the air bladders 44, 46 of the present invention can be secured to the prosthesis 22 by a number of different methods, and should not be limited to those discussed herein.

In the preferred embodiment, the bladders 44, 46 are also removable so that the amputee may use the foot prosthesis 22 without the air bladders. Moreover, because the present invention contemplates using a separate foot prosthesis structure in conjunction with the air bladders, the foot prosthesis can be used even when the bladders are deflated. This is significant because, in some situations, the bladders may become damaged or punctured. By permitting the amputee to continue to use the foot prosthesis, the amputee's activities are not entirely limited.

As can be seen in FIG. 2, the air bladders 44, 46 of the preferred embodiment also have tubes 52 extending therefrom, preferably from the centermost area, through which the air bladders can be inflated or deflated. In the preferred embodiment, each of these tubes 52 is connected to the air bladders 44, 46 in the center area of the sole 42 so that they are kept away from damage.

Also, in the preferred embodiment, the tubes 52 each have valves 54 (FIGS. 1 and 5) through which the air bladders 44, 46 can be inflated or deflated. The valves 54 can be of the type found on tires, a disk valve, or any number of a variety of valves suitable for this application, as is known in the art. The valves 54 enable the amputee to adjust the softness or firmness of the air bladders 44, 46 separately to accommodate the varying performance levels that may be desired by the amputee.

The present invention also contemplates a preferred range of volumes. Preferably, the volume in the heel bladder 44 is slightly larger than the volume in the toe bladder 46, as the heel bladder typically requires greater energy absorption and resiliency.

The volume and size of the air bladders also depends on the size of the prosthesis 20 being used. The present invention contemplates that the air bladders be of sufficient size to extend from the rearwardmost portion of the foot to the forwardmost portion of the toe, while having a width that is comparable to the sound foot of the amputee.

Figure 4:
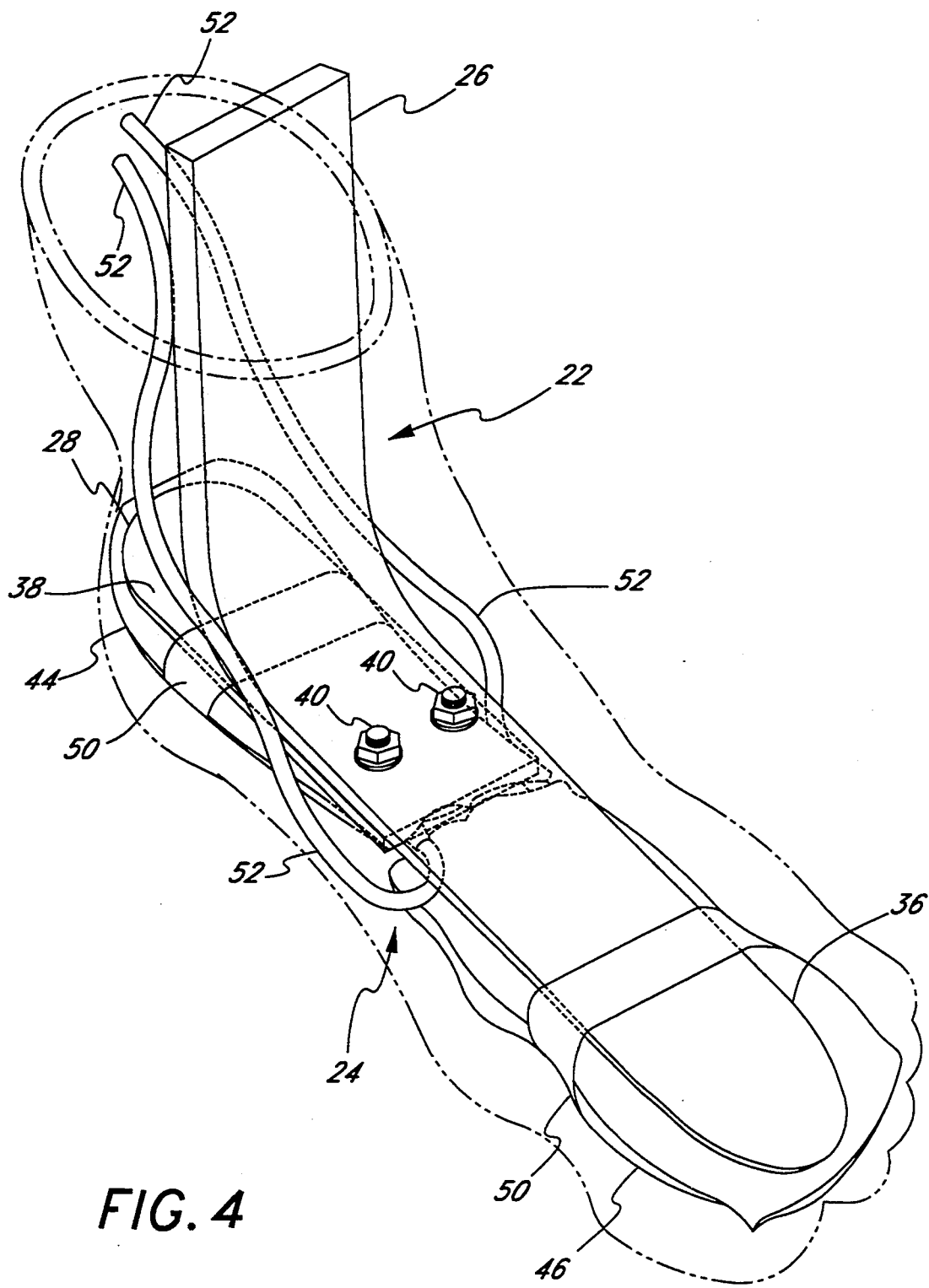
FIG. 4 is a perspective view of the prosthesis of FIG. 1 with the cosmesis shown in phantom.

As can be seen in FIGS. 1 and 4, the heel bladder 44 is positioned so that its rearwardmost portion extends slightly beyond the end of the heel portion 38 of the prosthesis structure, and the toe bladder 46 extends slightly beyond the frontwardmost end of the toe portion 36 of the prosthesis structure. This permits the air bladders to consistently provide good support and better leverage, both at the initial heel-strike and toe-load.

Referring to FIGS. 2 and 4, both the heel bladder 44 and toe bladder 46 are also positioned so that a small portion extends outward beyond the side edges of the prosthesis structure. This permits the air bladders to more faithfully recreate the response to lateral forces generated either by the ground terrain or the user. More specifically, the overhang at either side more accurately simulates the muscle and fleshy tissue on the sole of the human feet outward of the support bones.

The air bladders can also be adjusted slightly in height by increasing or decreasing the pressure in the bladders. By increasing the air pressure, the relative resiliency of the air bladders can be increased slightly which may be beneficial for amputees participating in rigorous sporting activities.

Figure 7:
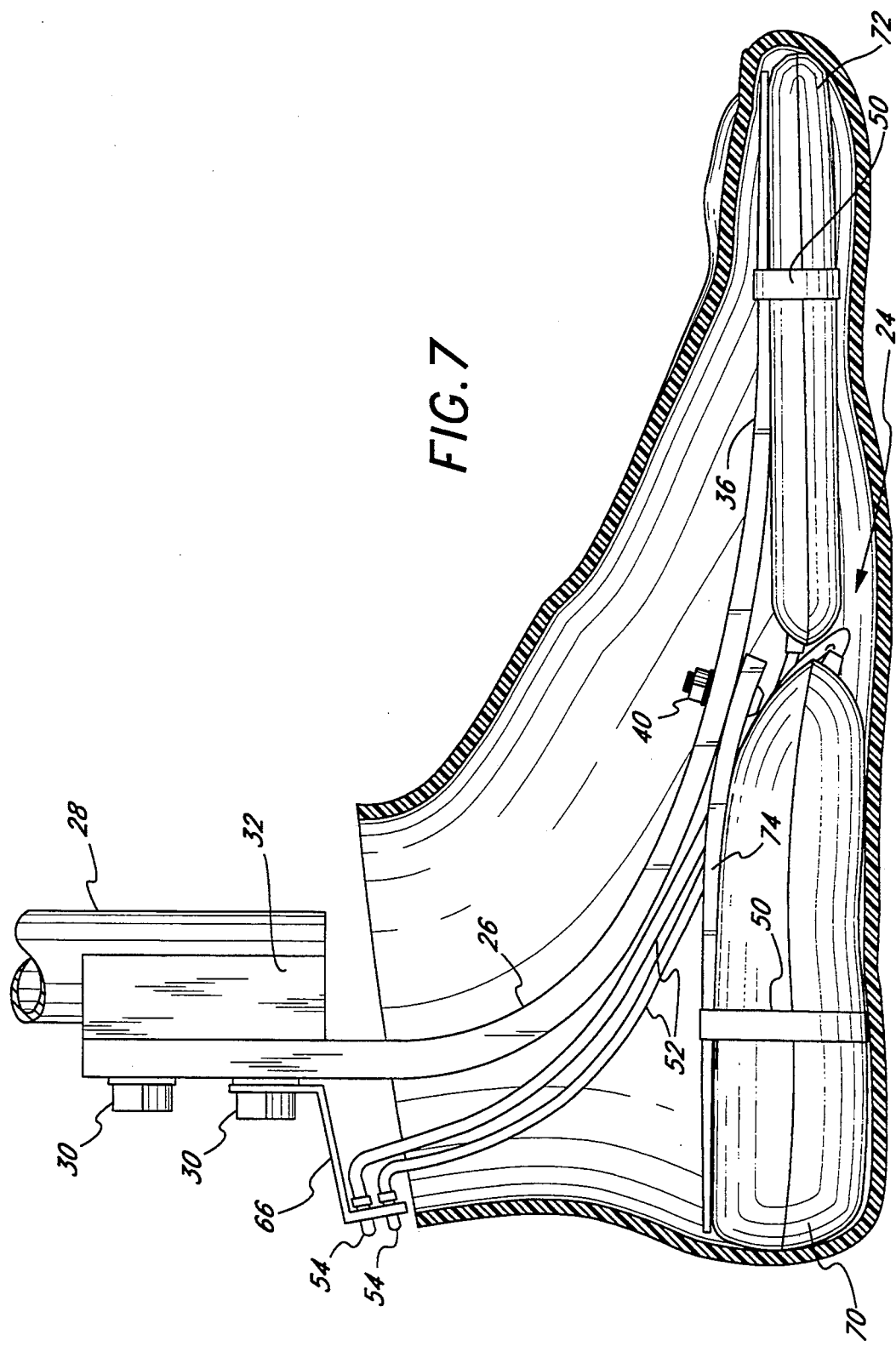
FIG. 7 is a side elevational view of an alternative embodiment of a foot prosthesis incorporating the air bladder system of the present invention.

The volume and size of the bladder is also a function of the intended use of the prosthesis. For instance, for geriatric use, air bladders of a size that are sufficient to provide energy absorption and resiliency at low to mid levels is sufficient. On the other hand, for individuals who participate in vigorous activities, a larger, more resilient air bladder may be desired. Indeed, it may be advantageous to use an air bladder system wherein the heel bladder 70 is significantly larger than the toe bladder 72, as shown in FIG. 7. The relative size of the air bladders corresponds to the need for high energy absorption, storage and resiliency at different points along the stride of the wearer.

In another embodiment (not shown), the bladders 44, 46 can be sealed tight without an adjustable valve and tube. In such case, the bladders are removable and interchangeable to permit various bladders of varying pressures to be utilized.

Bladder Construction

Figure 5:
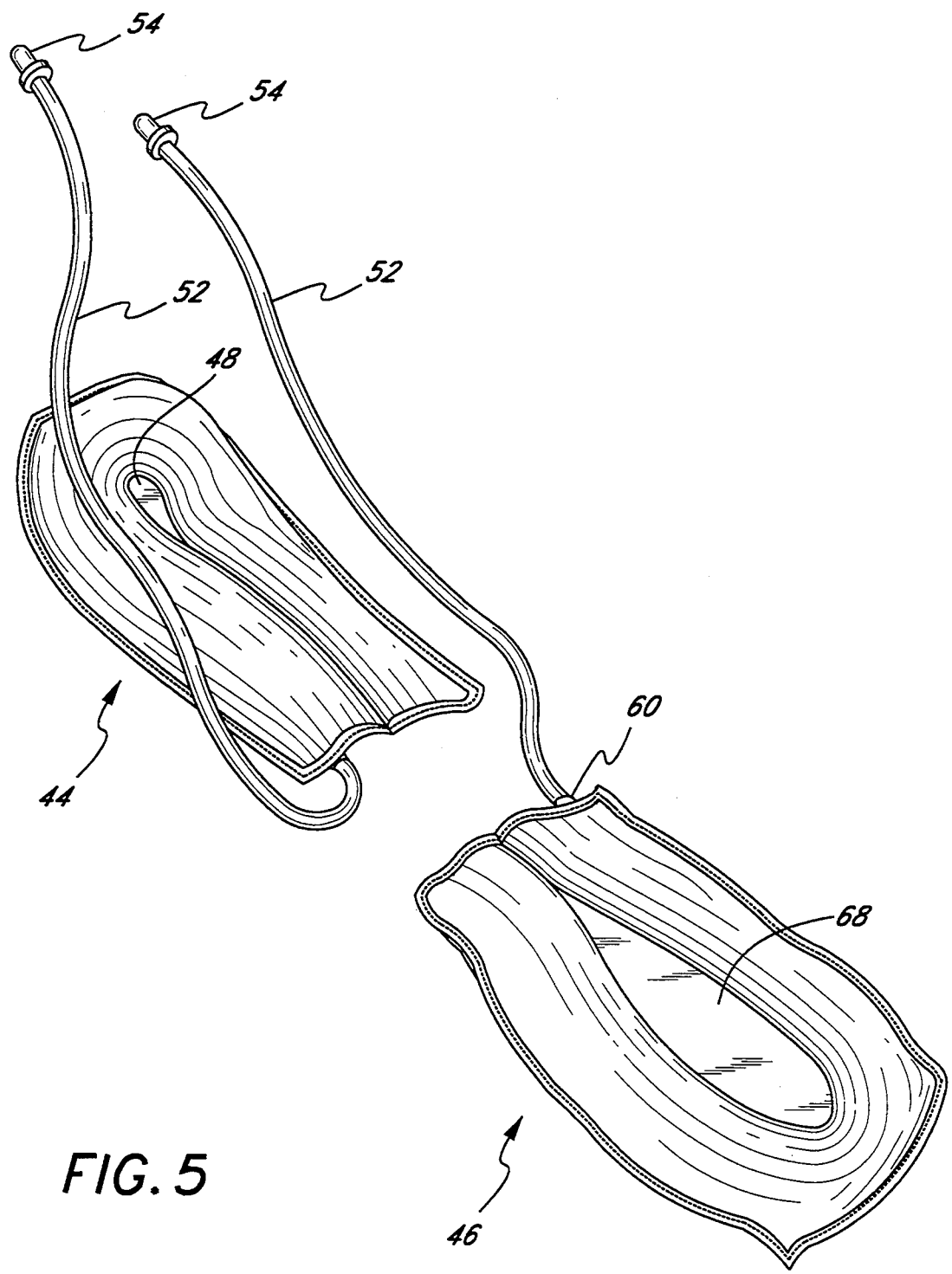
FIG. 5 is a perspective view of two preferred air bladders of the air bladder system of FIG. 1.
Figure 6:
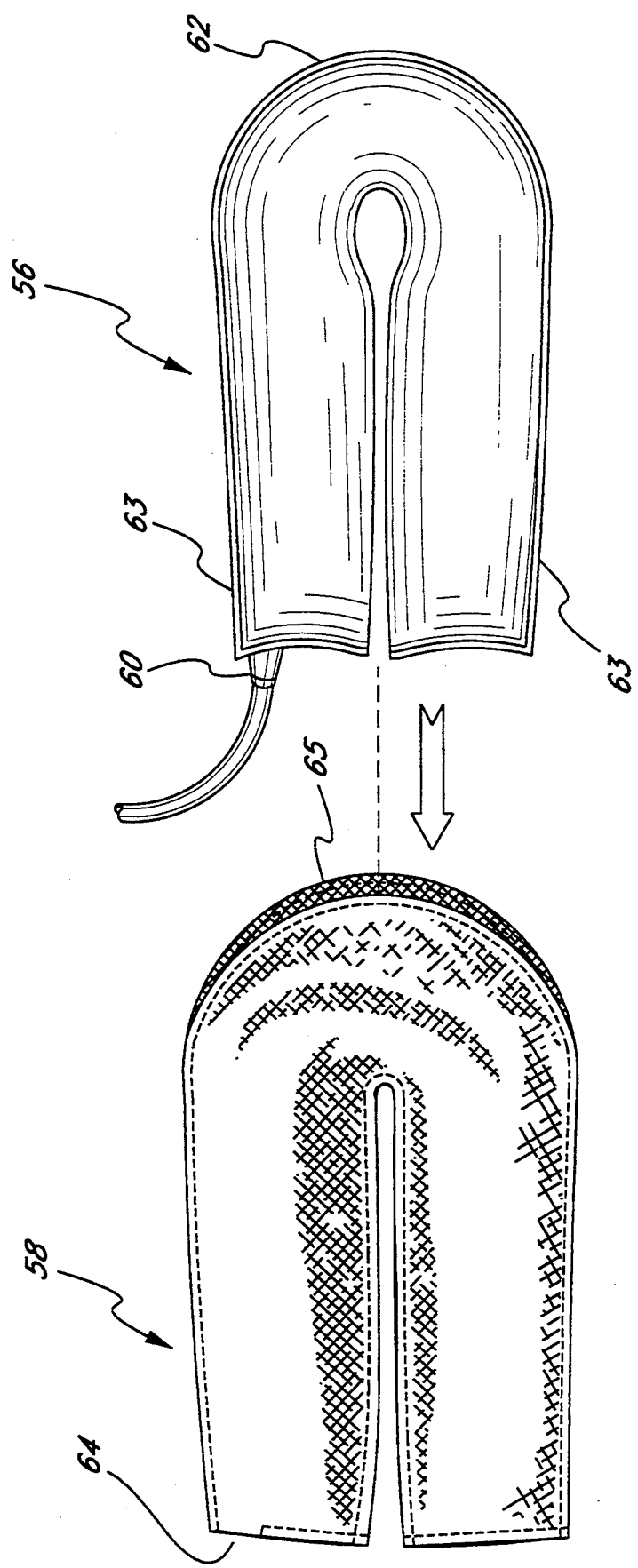
FIG. 6 is an exploded view of the components of one of the air bladders of FIG. 5.

The construction of the present air bladder is shown in FIGS. 5 and 6. While there may be a number of different ways to make the air bladders 44, 46, the preferred embodiment of the air bladders of the present invention are manufactured out of two materials, (1) a thin, flexible, suitably strong, lightweight moisture and vapor impervious material, such as polyurethane produced by the J. P. Stevens Elastomerics Company, and (2) a suitable strong stretch-resistant fabric material, such as ballistic nylon. The thin, flexible material is used to form an inside bag 56 and the stretch resistant material is used to form an outside bag 58 into which inside bag 56 is placed. Though other materials having similar characteristics can be used, and indeed are contemplated by the present invention, the remainder of the discussion will refer to the preferred materials, polyurethane and nylon. (Though materials having some elasticity can be used instead of nylon, elasticity is not necessarily a desired feature because of the tendency of the bladder to be too bouncy.) In the preferred embodiment, as shown in FIG. 6, an inner bag 56 is made of polyurethane and an outer bag 58 is made of ballistic nylon.

As shown in FIG. 6, the inner bag 56 is substantially an inflatable inner bladder sized to fit inside an outer bag 58 formed out of stretch resistant material. Though other shapes may provide the benefits discussed herein, the preferred embodiment utilizes U-shaped bladders. The U-shape configuration generally comprises an arcuate bottom end 62 joining two legs 63.

To form the inner bag 56, two pieces of material are heat stamped together by a stamp having the appropriate configuration. The stamping seals the two pieces of material together along the edges to prevent air from leaking therebetween, while at the same time, serving to cut the pieces into the proper shape. The two layers are otherwise not attached and enable air to pass into the inner bag 56 between the two layers. Though the bladders 44, 46 are preferably filled with air, they can also be adapted to be filled with $CO_2$ or other gases, or liquids or gels, such as water, silicon or the like.

During this process, a nipple 60 (FIG. 5 or 6) is inserted between the two layers along the perimeter of the material, such that the nipple extends outward from the perimeter. The nipple 60 is positioned in the inner bag 56 at the end of one of the legs 63 of the U-shape configuration, as shown in FIG. 5. Once positioned, the nipple 60 is then sealed to the inner bag 56 during the heat stamping process, although the nipple is covered so that the heat stamping device does not remove the nipple from the edge of the liner material.

The outer bag 58 into which the inner bag 56 is inserted is formed from two sheets of nylon, or other like stretch-resistant material, which are placed on top of each other. The stretch-resistant material is first cut into the same shape as the inner bag, which in the preferred embodiment is a U-shape configuration similar to configuration 56, except slightly larger, and sewn partially together around its perimeter. To make it easier to insert the inner bag 56 into the outer bag 58, the outer bag is left open along the arcuate bottom end 65, as shown in FIG. 6. A small opening 64 is also provided in the stitching to permit the nipple 60 to extend through the outer bag 58.

The inner bag 56 is then inserted into the outer bag 58, the legs 63 going in first, as shown in FIG. 6. Once the inner bag 56 is placed in the outer bag 58, the outer bag is sewn along the bottom end 65 to seal the inner bag in the outer bag. The nipple opening 64 is also stitched to seal the outer bag 58 around the nipple 60. A tube 52 is then placed onto the nipple 60 and sealed, which serves to inflate and deflate the air bladder.

As stated above, and as shown in FIGS. 1 and 5, the preferred embodiment of the present invention also utilizes a valve 54 attached at the end of each tube 52 through which the air pressure within the air bladder can be adjusted. Referring to FIG. 1, the valve 54 extending from the tube 52 can be secured to the prosthesis via a bar 66 extending from the bolts 30 which fasten the foot portion 26 to the pylon member 28, so that the valve can be easily accessed by the amputee. The valve 54 can also be secured to the lower end of the pylon 28 or other convenient location.

The air bladders 44, 46 of the present invention can also be manufactured from a single material, or a composite material, such as those consisting of both nylon and polyurethane, that is both vapor impervious and resistant to stretching. The air bladders can be made in the same fashion by placing two sheets of the material together. However, the sheets are heat stamped along the perimeter in a single step. The nipple 60 can be inserted between the two layers of material, as discussed above, and the materials can be heat sealed around the nipple to form an air-tight seal.

The present invention also contemplates utilizing a soft foam rubber cosmesis, as shown in FIG. 1, which covers the entire foot prosthesis structure and air bladder system. The cosmesis is provided with an opening so that the valve members extending from the tubes can be accessed without removing the cosmesis. A pad can also be positioned underneath the air bladder system to provide an additional cushion (not shown).

Operation

The bladders 44, 46 are advantageously formed such that at the moment that a bladder is compressed, the bladder is at a high-energy storage mode. As the load is lifted from the air bladder, pressure within returns to its previous level. Thus, the compression and release of pressure provides a unique combination of energy absorption, storage and release. In addition, the air bladders have a natural tendency to return to their original shape and configuration, which also facilitates the energy return and release characteristics, providing greater resilience and a more energetic response to compression.

In operation, the air bladders 44, 46 of the preferred embodiment of the present invention are advantageously positioned so as to eliminate unwanted migration of air from one end of the prosthesis to the other. Generally, as the amputee participates in normal walking, the heel bladder 44 is compressed due to the weight being exerted at the heel-strike, causing the pressure within the heel bladder to increase. As the pressure is increased, the air in the heel bladder 44 migrates to a point of lower pressure, which, in this case, is toward the front of the prosthesis 47. However, because the heel bladder 44 only extends halfway along the sole 43 of the prosthesis 20, the air does not migrate to the front 47 of the toe portion 36, which would otherwise cause the heel to flatten out. Thus, the separation of the heel bladder 44 and toe bladder 46 permits greater resiliency within the heel bladder.

Moreover, one skilled in the art can readily see that the separation of the toe bladder 46 from the heel bladder 44 also prevents migration backward from the toe end 47 to the heel end 45 of the prosthesis 20. This also prevents the toe bladder from flattening out during the toe-load and toe-off portions of the stride.

Some migration of air, however, is desired so that the heel bladder 44 can more readily absorb the impact of the initial strike. Because air is permitted to migrate at least to the center of the sole 42, in the preferred embodiment, the heel bladder 44 compresses slightly to enable the foot prosthesis 20 to roll from the heel-strike to mid-stance more smoothly. Then, as the amputee's weight shifts, and the foot rolls over to the mid-stance, the air is redistributed evenly, providing a smooth transition to mid-stance.

At mid-stance, the weight exerted on the prosthesis 20 is more or less uniformly distributed on the heel portion 38 and toe portion 36, causing the heel bladder 44 and toe bladder 46 to compress substantially uniformly. However, because of the general resiliency of the heel bladder 44 of the present invention, the energy released at the heel-strike portion of the stride facilitates the amputee's movement and shifting of weight from the heel-strike to the mid-stance. The resiliency tends to push the heel 38 upward, causing the weight of the amputee to shift forward to the front of the prosthesis 47. Thus, the heel bladder 44 facilitates a smooth roll over from heel-strike to mid-stance, and then to toe-load.

At this point, as the toe bladder 46 is compressed, the pressure within thereby increases as the toe bladder spreads both laterally outward and inward, much like the heel bladder 44 at heel-strike. The toe bladder 46, however, in the preferred embodiment, has a larger cavity 68, which provides a larger sweet spot for centering the load exerted on the toe portion 36. The effective resilient perimeter of the toe bladder 46 is therefore slightly larger, which in turn provides improved centering. The shape of the toe bladder 46 also corresponds to the natural foot, which tends to be wider at the toe portion 36 than the heel portion 38.

Next, as the amputee rolls over from the toe-load to toe-off, the resiliency of the toe bladder 46 facilitates its movement, completing the last phase of a natural stride. At this point, pressure is exerted onto the toe end 47 of the prosthesis, which in turn exerts pressure on the forwardmost end of the toe bladder 46. Because this pressure is isolated at the frontmost portion of the prosthesis 47, air within the toe bladder 46 normally migrates backward, away from the frontmost end of the toe.

To reduce the tendency of air to migrate away from the toe end 47 of the toe bladder 46, the toe bladder can be inflated to a higher pressure. Thus, to provide a more resilient toe-off, the amputee merely needs to increase the pressure in the toe bladder 46, which in effect extends the toe bladder outward at the front end 47 of the prosthesis. This would normally be helpful for higher levels of activity, such as running, jogging and sprinting.

As a general rule, by keeping the pressure in the bladders relatively low, the amputee can provide a softer, more cushioned feel, which improves the smoothness of the roll-over transition from heel to toe. On the other hand, the amputee can increase the pressure in the bladders to provide increased resiliency and energy storage and release capabilities, which provides the amputee with higher performance capabilities.

In general, the pressure within each of the air bladders ranges between 15 pounds to 55 pounds. By keeping the pressure at approximately 20 pounds, the amputee may experience a soft, easy rollover from heel-strike to toe-off. By increasing the pressure to approximately 30 pounds, the amputee may experience a relatively soft rollover with a slightly more firm, resilient response. By increasing the pressure to 50 pounds, the amputee will experience a firm to hard resilient response. Each of these levels or many others can be achieved to suit the activity levels of the amputee, as well as to suit the particular weight of the amputee.

For instance, an amputee can increase the pressure in the heel bladder 44 while maintaining a medium level of pressure in the toe bladder 46, which may be ideal for activities requiring higher resiliency upon heel impact, such as jogging. On the other hand, the amputee may want to increase the pressure in the toe bladder 46 to provide better resiliency in the toe 36, which may be necessary for activities involving sprinting, jumping or the like.

ALTERNATE EMBODIMENTS

The present invention can also come in different embodiments, wherein a foot prosthesis device having a slightly different structure can be utilized. Because the air bladders of the present invention can be made into virtually any shape, the air bladders may be shaped to conform to different prosthesis structures. For instance, as shown in FIG. 7, the large heel bladder 70 can be placed underneath the raised heel portion 74, and the smaller toe bladder 72 can be positioned underneath the toe portion 36. Moreover, each of the bladders 70, 72 can be tapered such that the shape of the bladders themselves conform to the shape of the bottom surface of the sole. One of ordinary skill in the art can readily see that any number of bladder shapes can be utilized to conform to any of the various shapes of foot prostheses available.

The present invention also contemplates utilizing a number of bladders on the sole of the foot prosthesis. In the preferred embodiment, two U-shape bladders 44, 46 positioned end-to-end are provided to offer the substantial advantages discussed. One of ordinary skill in the art can readily see that any number of bladders of varying sizes and shapes can also be provided to attain the same or substantially the same performance levels and results. For instance, multiple bladders can be positioned along the bottom of the sole of the foot prosthesis to form substantially the same U-shape configuration or other configurations along the perimeter of the sole.

The air bladders of the present invention are also not limited to the U-shape configuration disclosed in the preferred embodiment. In fact, the present invention contemplates a number of configurations providing the substantial benefits herein discussed.

Figure 8:
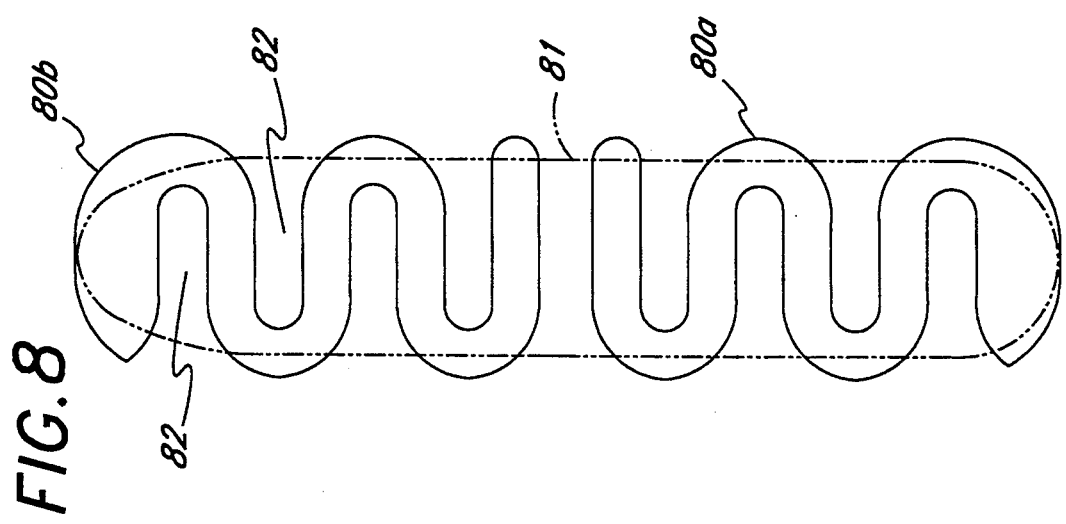

For instance, in FIG. 8, a serpentine configuration can be utilized to form air bladders 80a, 80b. Because the heel bladder 80a only extends halfway along the sole of the prosthesis 81 (shown in phantom), pressure exerted at the heel strike does not migrate to the toe bladder in 80b, which would otherwise cause the heel to flatten out. The advantage of the serpentine configuration is that the air bladders 80a, 80b can expand substantially within transverse gaps 82 to provide better energy storage and release, and improved centering.

Figure 9:
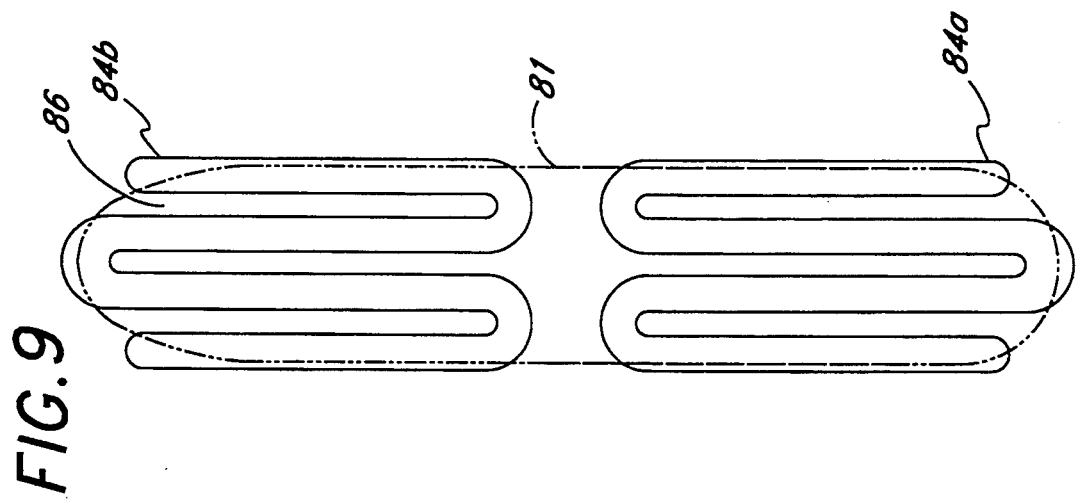

In a similar manner, as shown in FIG. 9, a further serpentine arrangement of two air bladders 84a, 84b provides longitudinal gaps 86 which allow the air bladders to expand substantially within, providing better energy storage and release, and improved centering. Once again, the heel bladder 84a and the toe bladder 84b are separate units which respond and provide feedback to the wearer separately.

Figure 10:
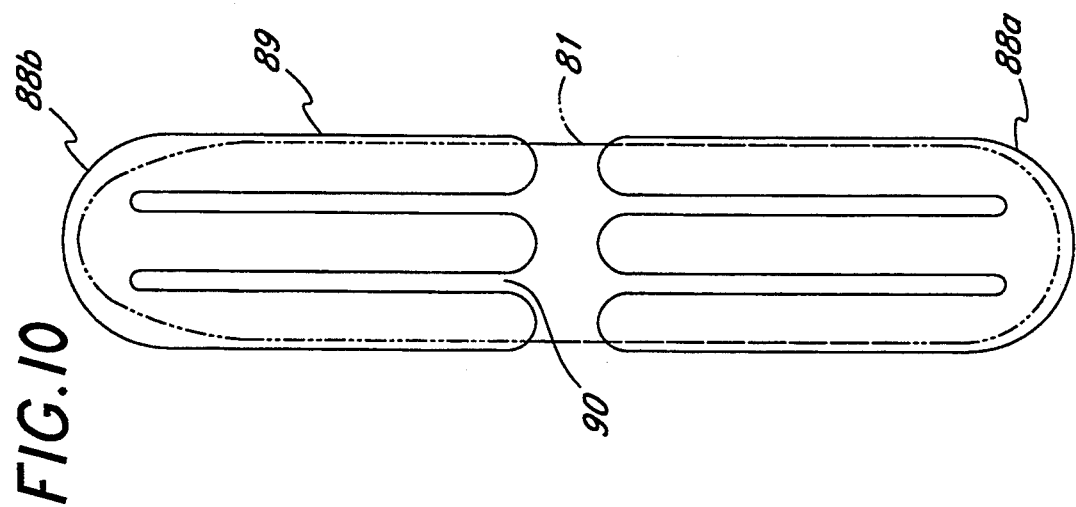

In still a further embodiment of the air bladder system of the present invention, FIG. 10 shows a heel bladder 88a and a toe bladder 88b in the shape of multiple tine 89 inwardly facing forks. As before, the bladders 88a,b are separated across the midsection of the prosthesis to provide separate toe and heel response characteristics. The longitudinal tines 89 of the air bladders overhang the side edges of the prosthetic device 81 to provide good transverse or lateral response, as was described for the U-shaped bladders of the preferred embodiment. Additionally, gaps 90 between the longitudinal tines 89 provide regions into which the air bladders 88a, 88b can expand within to provide better energy storage and release, and improved centering.

As shown in FIG. 11, a further embodiment of the air bladder system of the present invention utilizes a heel bladder 92a and a toe bladder 92b both having a longitudinal middle portion 94 connecting a plurality of outwardly extending transverse tubes 96 separated by gaps 98. The independent walking or running response characteristics of the separate heel member 92a and toe member 92b are once again noted. In addition, the transverse tubes 96 may expand into the gaps 98 to provide better energy storage and release. The lateral ends of each tube 96 extends outward from the side edge of the prosthetic device 81 enhancing transverse foot prosthesis response by allowing sideways rollover.

In FIG. 12, two upholstered single piece bladders 100a, 100b are separated by a central gap 102. The bladders 100 are preferably manufactured from polyurethane in a heat stamping process, as described above for the preferred embodiment, and comprise points of connection 104 between an upper surface 106 and a lower surface 108, as more clearly shown in FIG. 12a. The points of connection 104 prevent the air bladders 100 from becoming too high centered after inflation. The points of connection 104 also prevent the bladders 100 from becoming lopsided when weight is applied on one side of the prosthetic foot.

FIG. 13 shows a further embodiment of the air bladder system of the present invention. A plurality of dome-shaped bubbles 110 are affixed to a lower pad 112, as shown in FIG. 13a. The bubbles 110 provide independent resilient response, and may be distributed underneath the prosthetic foot in an optimum manner. In one arrangement, there are ten bubbles 110 distributed in two lines of five along the longitudinal axis of the foot and one bubble at each end of the foot.

The present invention and its various embodiments are illustrated and described herein. However, the scope of the present invention should not be limited specifically to these embodiments as other embodiments that encompass the inventive concepts discussed herein are contemplated by the claims that follow.

What is claimed is:

1. A foot prosthesis securable to a socket mounted to the stump of an amputee for providing support for an amputee relative to the ground, comprising:

a pylon member adapted to be secured to said socket;

a foot portion secured to said pylon member and extending relatively downward therefrom, said foot portion being flexible to store and release energy, and having a sole extending from the heel end to the toe end;

a first bladder secured to the bottom of said sole, said first bladder extending only partially between said heel end and said toe end such that the migration of air from said heel end to said toe end is eliminated, said first bladder being adapted to absorb, store and release energy; and a second bladder secured to the bottom of said sole, said second bladder extending only partially between said heel end and said toe end such that the migration of air from said toe end to said heel end is eliminated, said second bladder being adapted to absorb, store and release energy, wherein each of said bladders includes a pair of arm portions and a connecting portion, each of said bladders defining a cavity between said pair of arm portions such that said bladders expand laterally outward and laterally inward toward said cavity.

2. The foot prothesis of claim 1, wherein said first and second bladders have a U-shape configuration.

3. The foot prosthesis of claim 1, wherein said first bladder extends from the heel end of said sole to about half-way between said heel end and said toe end.

4. The foot prosthesis of claim 1, wherein said second bladder extends from said toe end of said sole to about half-way between said toe end and said heel end.

5. The foot prosthesis of claim 1, wherein said first and second bladders are made of an inner layer of polyurethane and an outer layer of nylon material.

6. The foot prosthesis of claim 1, wherein said first and second bladders are adjustably inflatable.

7. The foot prosthesis of claim 1, wherein said first and second bladders each have a tube extending therefrom, wherein a valve is secured at the end of each of said tubes to permit said first and second bladders to be adjustably inflated.

8. A foot prosthesis adapted to be secured to a socket mounted to the stump of an amputee for providing support for an amputee relative to the ground, comprising:
- a substantially rigid pylon member adapted to be secured to said socket;
- a foot portion secured to said substantially rigid pylon member and extending relatively downward therefrom, said foot portion being flexible to store and release energy, said foot portion having a curvilinear ankle section and a toe section extending relatively forward from said ankle section, said ankle section and said toe section forming a single continuous unit, and a separate toe section secured to said continuous unit extending relatively rearward, said foot portion having a sole extending from the heel end to the toe end;
- a heel bladder secured to the bottom of said heel section, said heel bladder extending approximately from said heel end to about midway between said heel end and said toe end such that the migration of air from said heel end to said toe end is eliminated, said heel bladder also having a cavity therein such that when weight is placed on said heel bladder, said heel bladder expands laterally outward and laterally inward toward said cavity, so as to give the amputee the sensation of being low-centered rather than high-centered; and
- a toe bladder secured to the bottom of said toe section, said toe bladder extending approximately from said toe end to about midway between said toe end and said heel end such that the migration of air from said toe end to said heel end is eliminated, wherein said toe bladder has a cavity therein such that when weight is placed on said toe bladder, said toe bladder expands laterally outward and laterally inward toward said cavity so as to give the amputee the sensation of being low-centered rather than high-centered.

9. The foot prosthesis of claim 8, wherein said heel bladder and said toe bladder have a U-shape configuration.

10. The foot prosthesis of claim 8, wherein said heel bladder and said toe bladder are adjustably inflatable.

11. A foot prosthesis, comprising:
- a pylon member adapted to be secured to a socket mounted to the stump of an amputee;
- a foot portion being flexible to store and release energy, said foot portion having a sole extending from the heel end to the toe end; and
- two or more bladders positioned on the bottom of said sole, said bladders being arranged in such a manner as to eliminate the migration of air between the heel end and toe end of said prosthesis, wherein said two or more bladders each have a U-shape configuration, including a pair of arm portions and a connecting portion, each of said two or more bladders defining a cavity between said pair of arm portions such that said bladders expand laterally outward and laterally inward toward said cavity.

12. The foot prosthesis of claim 11, wherein said two or more bladders each are adjustably inflatable.

13. A foot prosthesis, comprising:
- a prosthetic foot portion being flexible to store and release energy, said foot portion having a sole extending from the heel end to the toe end; and
- two or more bladders positioned on the bottom of said sole, said bladders being adapted to absorb, store and release energy, each of said bladders including a pair of arm portions and a connecting portion, said bladders each defining a cavity between said pair of arm portions to permit each of said bladders to expand laterally outward and laterally inward toward said cavity so as to improve the energy storage and release capabilities of said bladders, and to provide the amputee with a sensation of being low-centered rather than high-centered.

14. The foot prosthesis of claim 13, wherein said two or more bladders are made of a polyurethane inner lining and a nylon outer lining.

15. The foot prosthesis of claim 13, wherein said two or more bladders are adjustably inflatable.

16. A foot prosthesis, comprising:
- a foot prosthetic portion having a sole extending from the heel end to the toe end; and
- two or more air bladders secured to the bottom of said sole, said two or more bladders being arranged such that said bladders extend from the rearward most perimeter of said heel end to the forward most perimeter of said toe end, such that said bladders provide a smooth rollover from heel to toe, each of said bladders extending no more than approximately half the distance between said heel end and said toe end, wherein each of said bladders includes a pair of arm portions and a connecting portion, each of said bladders defining a cavity between said pair of arm portions such that said bladders expand laterally outward and laterally inward toward said cavity.

* * * * *